United States Patent
Springer et al.

(10) Patent No.: US 8,835,485 B2
(45) Date of Patent: Sep. 16, 2014

(54) PREVENTION AND TREATMENT OF SARCOPENIA

(75) Inventors: Jochen Springer, Berlin (DE); Stefan Anker, Berlin (DE); Andrew Coats, Norwich (GB); John Beadle, Essex (GB)

(73) Assignee: PsiOxus Therapeutics Limited, London (GB)

( * ) Notice: Subject to any disclaimer, the term of this patent is extended or adjusted under 35 U.S.C. 154(b) by 0 days.

(21) Appl. No.: 13/263,430

(22) PCT Filed: Apr. 29, 2010

(86) PCT No.: PCT/GB2010/000855
§ 371 (c)(1),
(2), (4) Date: Dec. 6, 2011

(87) PCT Pub. No.: WO2010/125348
PCT Pub. Date: Nov. 4, 2010

(65) Prior Publication Data
US 2012/0095070 A1 Apr. 19, 2012

(30) Foreign Application Priority Data
Apr. 29, 2009 (GB) .................................. 0907350.3

(51) Int. Cl.
*A61K 31/40* (2006.01)
*A61K 31/13* (2006.01)
*A61K 31/404* (2006.01)
*A61K 31/133* (2006.01)

(52) U.S. Cl.
CPC ............. *A61K 31/404* (2013.01); *A61K 31/133* (2013.01)
USPC .......................................... 514/416; 514/670

(58) Field of Classification Search
None
See application file for complete search history.

(56) References Cited

U.S. PATENT DOCUMENTS

| 2002/0165263 A1 | 11/2002 | Dinan et al. |
| 2007/0021421 A1 | 1/2007 | Hampton |
| 2010/0292270 A1 | 11/2010 | Cavalla |

FOREIGN PATENT DOCUMENTS

| WO | WO 00/21509 A2 | 4/2000 |
| WO | WO 03/006001 A1 | 1/2003 |
| WO | WO 2006/102476 A2 | 9/2006 |
| WO | WO 2008/068477 A1 | 6/2008 |
| WO | WO 2008068477 A1 * | 6/2008 |

OTHER PUBLICATIONS

Thomas, Clinical Nutrition 2006 (26) 389-399 published Mar. 2007.*
Bennett et al, "A randomized, double-blind, placebo-controlled study of growth hormone in the treatment of fibromyalgia," American Journal of Medicine, vol. 104, No. 3, Mar. 1998, pp. 227-231.
Cachexia, Wikipedia, downloaded 2011.
Cruz-Jentoft et al, "Sarcopenia: European consensus on definition and diagnosis," Age and Ageing 2010; 39: 412-423.
Cziraki et al: "Application of the chronopharmacological methods in clinicopharmacological studies. The effect of bopindolol on the diurnal rhythm of blood pressure in patients suffering from essential hypertension," Pharmacological Research, vol. 25, May 1, 1992, p. 188.
Evans, "Skeletal muscle loss: cachexia, sarcopenia, and inactivity," The American Journal of Clinical Nutrition 2010; 91 (suppl): 1123S-7S.
Evans & Campbell, "Sarcopenia and Age-Related Changes in Body Composition and Functional Capacity," Symposium: Aging and Body Composition: Technological Advances and Physiological Interrelatioships, American Institute of Nutrition, 1993, 465-468.
Fearon, "Myopenia—a new universal term for muscle wasting," J Cachexia Sarcopenia Muscle (2011) 2: 1-3.
Fibromyalgia, Wikipedia, downloaded 2011.
Morley: "Weight loss in older persons: New therapeutic approaches," Current Pharmaceutical Design, vol. 13, No. 35, 2007, pp. 3637-3647.
Muscaritoli et al: "Consensus definition of sarcopenia, cachexia and pre-cachexia: joint document elaborated by Special Interest Groups (SIG) "cachexia-anorexia in chronic wasting diseases" and nutrition in geriatrics," Clinical Nutrition, vol. 29, No. 2, Apr. 2010, pp. 154-159.
Sarcopenia, Wikipedia, downloaded 2011.
Scott et al., "The epidemiology of sarcopenia in community living older adults: what role does lifestyle play?," J Cachexia Sarcopenia Muscle (2011) 2: 125-134.
Von Haehling et al., "An overview of sarcopenia: facts and numbers on prevalence and clinical impact," J Cachexia Sarcopenia Muscle (2010) 1: 129-133.
Wyller et al: "Treatment of Chronic Fatigue and Orthostatic Intolerance with Propranolol," Journal of Pediatrics, vol. 150, No. 6, May 19, 2007, pp. 654-655.
Lesser, "A phase III randomized study comparing the effects of oxandrolone (Ox) and megastrol acetate (Meg) on lean body mass (LBM), weight (wt) and quality of life (QOL) in patients with solid tumors and weight loss receiving chemotherapy," ASCO abstract, Jun. 2, 2008, 3 pages.
Pending claims, U.S. Appl. No. 12/312,756, 2 pages, Sep. 2, 2009.
Soriano et al., "The Proportional Venn Diagram of Obstructive Lung Disease," Chest 124, 474-81, Aug. 2003.

* cited by examiner

*Primary Examiner* — Jeffrey S. Lundgren
*Assistant Examiner* — Michael Schmitt
(74) *Attorney, Agent, or Firm* — Knowles Intellectual Property Strategies, LLC

(57) ABSTRACT

The present invention provides a means for prevention and treatment of sarcopenia by administration of a substance that both reduces the sensibility of beta-adrenergic receptors and of 5-HT1a receptors. (S)-pindolol, (S)-propanol, tertalol, or bopindolol are preferred for this purpose.

8 Claims, 4 Drawing Sheets

PREVENTION AND TREATMENT OF SARCOPENIA

FIELD OF THE INVENTION

Figure 1:
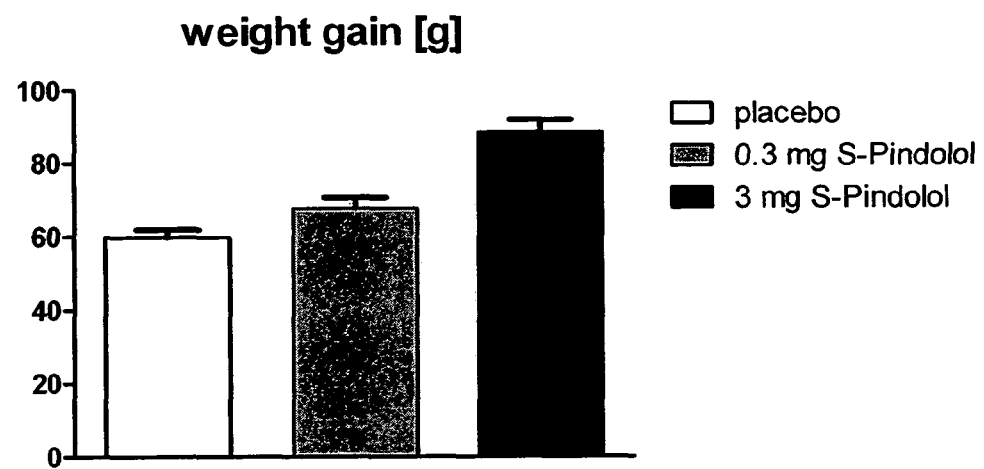

The present invention lies in the field of compounds or methods for the treatment of sarcopenia.

Sarcopenia is defined as the loss of muscle mass associated with aging, which is increasingly recognized as having important consequences in old age, because it may be associated with weakness, disability and morbidity (Frontera W R et al., 1991, Baumgartner et al., 1998, Hughes V A et al., 2001). The prevalence of sarcopenia increases from 13-24% among people under 70 to more than 50% among those over 80 (Baumgartner et al., 1998). Muscle weakness associated with sarcopenia is known to be associated with fatigue, a reduced ability to perform the tasks required for independent living and an increased risk of bony fractures, such as but not limited to fractured neck of femur (Lloyd B D, et al, Recurrent and injurious falls in the year following hip fracture: a prospective study of incidence and risk factors from the Sarcopenia and Hip Fracture study. J Gerontol A Biol Sci Med Sci. 2009 May; 64(5):599-609)

Sarcopenia is a distinct syndrome from starvation and the cachexia syndrome (Roubenoff et al., 1997), which has recently been defined by a consensus group as "at least a 5% loss of edema-free body weight during the previous 12 months or less. The time frame may be disease specific and is likely to be shorter in cancer (3-6 months) and longer in chronic kidney or heart failure or COPD (12 months)" (Evans et al., 2008).

In contrast to cachexia, patients suffering from sarcopenia may be weight stable, but show a distinct loss of muscle mass, while at the same time typically the fat mass increases.

Current experimental treatment regimes for sarcopenia utilize nutritional approaches, exercise training, appetite stimulants and anabolic compounds such as testosterone, but the effects of previously described treatments are not satisfactory (Morley 2007).

SUMMARY OF THE INVENTION

The present invention provides a method for treating or preventing sarcopenia by administering compounds that are antagonists or partial agonists of both beta-adrenergic receptors and of 5-HT1a receptors. Sarcopenia is seen where in an elderly subject muscle bulk is reduced and as such any person over the age of 60 years might be considered at risk for developing sarcopenia. Preventive strategies might therefore be usefully targeted at anyone over the age of 60 years and especially where muscle bulk is reduced or exercise capacity limited already. These features could readily be determined by simple medical history taking and examination by a medical practitioner, so that identification of a population at risk for sarcopenia would be a uncomplicated task for one skilled in the art.

Class I sarcopenia has been defined as an appendicular lean body mass index (ALBMI) < or =6.44 kg·m (−2) (appendicular lean body mass/height) (Messier V, Karelis A D, Lavoie M E, Brochu M, Faraj M, Strychar I, Rabasa-Lhoret R. Metabolic profile and quality of life in class I sarcopenic overweight and obese postmenopausal women: a MONET study. Appl Physiol Nutr Metab. 2009 February; 34(1):18-24.) This definition requires scanning of the legs and/or arms to determine muscle bulk. It has also been argued that these scans may not be necessary and that sarcopenia can be defined by measuring anthropometric measurements like arm muscle circumference and calf circumference to determine a below normal amount of limb skeletal muscle (Bauer J M, Kaiser M J, Sieber C C. Sarcopenia in nursing home residents. J Am Med Dir Assoc. 2008 October; 9(8):545-51). A working definition has been given which identifies sarcopenia when skeletal muscle mass in an older subject is more than 2 standard deviations below the mean for healthy younger adults (Baumgartner R N, Koehler K M, Gallagher D, et al (April 1998). "Epidemiology of sarcopenia among the elderly in New Mexico". Am. J. Epidemiol. 147 (8): 755-63)

(S)-pindolol, (S)-propranolol, (S)-carteolol, (S)-penbutolol, (S)-alprenolol, tertatolol, (S)-tertatolol, mepindolol, (S)-mepindolol, bopindolol and (S)-bopindolol are preferred compounds for this purpose. (S)-pindolol is a particularly preferred compound.

According to the present invention, (S)-pindolol [also known as (−)-pindolol, S(−)-pindolol, S-(−)-1-(1H-indol-4-yloxy)-3-(1-methylethylamino)propan-2-ol], and (S)-propranolol [also known as (−)-propranolol, S(−)-propranolol, (S)-1-isopropylamino-3-(1-naphthyloxy)-2-propanol] which both have affinity for both beta-adrenergic receptors and 5-HT1a receptors, are considered to have beneficial effects in subjects suffering from or at risk of sarcopenia.

It is considered that the preferred compounds produce reduced alteration in blood pressure compared with a conventional beta-blocker, which reduces blood pressure. It is also considered that the preferred compounds may reduce fatigue.

DETAILED DESCRIPTION OF THE INVENTION

This invention envisages the use of any substance that interacts with both the beta-adrenoceptor and the 5-HT1a receptor as either an antagonist or a partial agonist.

Beta-adrenoceptor antagonists have been claimed to be useful in the treatment of cachexia according to EP99947762, the contents of which are included by reference. This patent refers to a method of treating weight loss due to underlying disease by the administration of an agent which reduces sympathetic nervous system activity. WO2006102476 describes combinations of beta adrenergic antagonists and anti-inflammatory agents, such as NSAIDs (non-steroidal anti-inflammatory agents). The racemic forms of pindolol and propranolol are specifically mentioned in these patents, although the utility of the enantiomers is not mentioned. WO 2008/068477 relates to treatment of cachexia but does not refer to sarcopenia.

As used herein, and as would be understood by the person skilled in the art, the enantiomeric forms of racemates refer to compositions consisting substantially of a single isomer, i.e. substantially free of the other isomer, containing at least 90% of such single isomer, or preferably at least 95% of such single isomer, or more preferably at least 98% of such single isomer.

Pindolol and propranolol are used in the treatment of hypertension and angina as the racemic substances, RS pindolol and RS propranolol, due mainly to their beta-adrenergic receptor activity. The pharmacological properties of the R-form of pindolol differ from those of the S-enantiomer. In addition to an affinity for beta adrenergic receptors, (S)-pindolol also has affinity for 5-HT1a receptors in a similar dose range. It has recently been reported (WO2006030306) that (S)-pindolol produced no alteration in blood pressure in a majority of healthy subjects whereas a similar dose of racemic pindolol had the effect of reducing diastolic blood pressure. Thus, (S)-pindolol is behaving unlike a conventional beta-blocker, which reduces blood pressure.

(S)-propranolol interacts enantioselectively with the 5HT-1a receptor (J. Pharm. Pharmacol. 39, 664-666, (1987)) and functional tests have confirmed that (S)-propranolol but not (R)-propranolol blocked the suppressant effects of 5-HT1a agonists on dorsal raphe neuronal firing (Eur J. Pharmacol. 1986 Sep. 9; 128(3):295-8). The different effects of (S)- and (R)-propranolol have also been observed in forearm blood flow experiments (J Cardiovasc Pharmacol. 1995 February; 25(2):268-72).

The present invention utilizes dual-acting compounds to interact with both beta-adrenergic receptors and 5-HT1a receptors and as a result to provide the means for the treatment or prevention of sarcopenia, preferably while avoiding a common side effect of beta-adrenergic antagonists, namely fatigue. Both antagonists and partial agonists of these receptors are envisaged by the invention. Partial agonists of the beta-adrenergic receptor have been characterised as having intrinsic sympathomimetic activity. Preferred embodiments of the invention include the isomers (S)-pindolol, (S)-propranolol, (S)-carteolol, (S)-penbutolol or (S)-alprenolol as well as the racemic tertatolol, mepindolol or bopindolol or pharmaceutically acceptable salts thereof. The inventions also envisages the utilisation of the S-enantiomers of tertatolol, mepindolol or bopindolol or pharmaceutically acceptable salts thereof.

The treatment is considered to be useful in treating or preventing one or more of the following associated with sarcopenia: loss of skeletal muscle mass; muscle weakness; fatigue; disability; morbidity. The treatment is also considered to be useful for increasing the strength of skeletal muscle in sarcopenia; reducing the risk of bony fractures in patients with sarcopenia.

The treatment is also considered to be useful in the prevention or treatment of muscle wasting associated with ageing; disuse atrophy; muscle weakness associated with muscle wasting associated with ageing; muscle weakness associated with disuse atrophy; prevention or secondary prevention of bony fractures associated with muscle wasting or weakness associated with ageing or sarcopenia.

The treatment is also considered to be useful for improving exercise ability; to increase lean muscle mass; improve survival or to improve quality of life as assessed by a validated quality of life questionnaire instrument.

The treatment is considered to be useful in patients with diagnosed sarcopenia or in those above the age of 60 at risk of developing sarcopenia; or more generally in the elderly, for example over the age of 65, 70 or 80 years.

It is considered that the treatment may lead to a reduction in the number of unplanned hospital admissions, both for an individual patient and for a population.

One of the side effects of beta-adrenoceptor antagonists is fatigue. This is a particular problem in sarcopenia. Reluctance to prescribe these agents may derive from concerns about their association with symptoms of fatigue. According to Ko et al (JAMA 2002; 288:351-7), an increase of 15% in reported symptoms of fatigue is found in heart failure patients treated with beta-adrenoceptor antagonists.

In one aspect, compounds of the invention are particularly useful in the treatment of sarcopenia compared to other drugs which act solely as beta-adrenergic antagonists because, for example in humans, fatigue is either not increased or in some cases may be reduced, while efficacy against sarcopenia is maintained. For example, we consider that the dual action agent s-pindolol is likely to be less subject to the side-effect of increasing fatigue. Preferably, in the subject treated, fatigue is reduced. Fatigue in general is a common health complaint. It is, however, one of the hardest terms to define, and a symptom of many different conditions, as discussed in Macintosh B R, Rassier D E. What is fatigue? Can J Appl Physiol. 2002 February; 27(1):42-55. (Review).

In another aspect, compounds of the invention are effective against sarcopenia in the absence of an effect on blood pressure, for example in humans, or in the subject treated.

Sarcopenia has a high prevalence in the older population and is a major cause of morbidity leading to an economic burden of $18.5 billion USD in the USA alone (Janssen et al. J Am Geriatr Soc. 2004 January; 52(1):80-5). Treatment of sarcopenic patients with S-Pindolol is considered to improve their skeletal muscle mass, and as a result improve their general well being and reduce fatigue as well as morbidity. Particularly the preferential effect of S-Pindolol on fast twitch fibers is considered to be very useful, as these fibers show a higher degree of atrophy in sarcopenia (Macaluso A, De Vito J. Muscle strength, power and adaptations to resistance training in older people. Eur J Appl Physiol. 2004 April; 91(4): 450-72.) (Basu et al. J Nutr Health Aging. 2002; 6(5):336-41.)

As used in this invention, the usual doses of (S)-pindolol will be in the range of 2.5 mg to 50 mg daily (for a human) in single or divided doses, depending upon the therapeutic response and the pharmaceutical form. The usual doses of (S)-propranolol will be in the range of 2.5 mg to 100 mg daily in single or divided doses, depending upon the therapeutic response and the pharmaceutical form. The dose may be similar to or below that which has routinely been used for the treatment of high blood pressure or angina.

Various pharmaceutical presentations are possible, including (but not limited to) tablets, capsules, liquid, oral solutions and suspensions, parenteral solutions, buccal melt, intravenous solution or topical application form. Pharmaceutical formulations for oral use in which the active substance is released in a controlled and slower fashion such that the treatment may be administered less frequently are included.

The treatment may be administered in combination with a further pharmaceutically active agent, for example an angiotensin converting enzyme inhibitor, an angiotensin receptor antagonist, an aldosterone antagonist, a myostatin inhibitor, megestrol acetate, an appetite-stimulating steroid, nutritional support or a Ghrelin agonist. Examples of such compounds are well known to those skilled in the art, for example from standard reference texts such as Martindale The Complete Drug Reference, 35$^{th}$ Edition 2007, RPS Publishing.

A further aspect of the invention provides a pharmaceutical composition or kit of parts comprising a pharmaceutically acceptable carrier, a combined beta-adrenergic antagonist and 5-HT1a partial agonist or antagonist as defined in any one of claims 1 to 8 and an angiotensin converting enzyme inhibitor, an angiotensin receptor antagonist, an aldosterone antagonist, a myostatin inhibitor, megestrol acetate, an appetite-stimulating steroid, nutritional support or a Ghrelin agonist.

A still further aspect of the invention provides a pharmaceutical composition or kit of parts according to the preceding aspect of the invention for use in medicine.

A still further aspect of the invention provides a pharmaceutical composition or kit of parts according to the invention for use in treating or preventing sarcopenia or loss of skeletal muscle mass associated with sarcopenia; fatigue associated with sarcopenia; disability associated with sarcopenia; morbidity associated with sarcopenia; muscle weakness associated with sarcopenia; or to increase the strength of skeletal muscle in sarcopenia or to reduce the risk of bony fractures in a patient with sarcopenia; or for the prevention or treatment of muscle wasting associated with ageing; muscle weakness associated with muscle wasting associated with ageing; disuse atrophy; muscle weakness associated with disuse atrophy; or for the prevention or secondary prevention of bony fractures associated with muscle wasting or weakness associated with ageing or sarcopenia.

The invention is intended for the treatment of mammals, including humans and domestic and farm animals.

The invention is now further described by reference to the following, non-limiting Figures and Examples.

FIGURE LEGENDS

FIG. 1: weight gain during treatment. Plac vs 0.3 mg/kg/d: p=0.06, Plac vs 3 mg/kg/d: p=0.0002, 0.3 mg/kg/d vs 3 mg/kg/d: p=0.0021.

Figure 2:
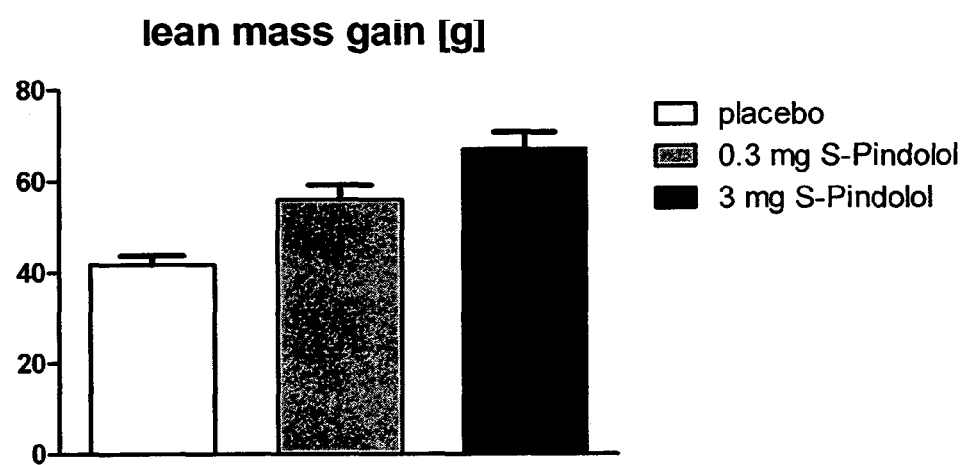

FIG. 2 gain of lean mass during treatment. Plac vs 0.3 mg/kg/d: p=0.0066, Plac vs 3 mg/kg/d: p=0.0009, 0.3 mg/kg/d vs 3 mg/kg/d: p=0.057.

Figure 3:

FIG. 3: body weight at baseline, p=0.82.

Figure 4:
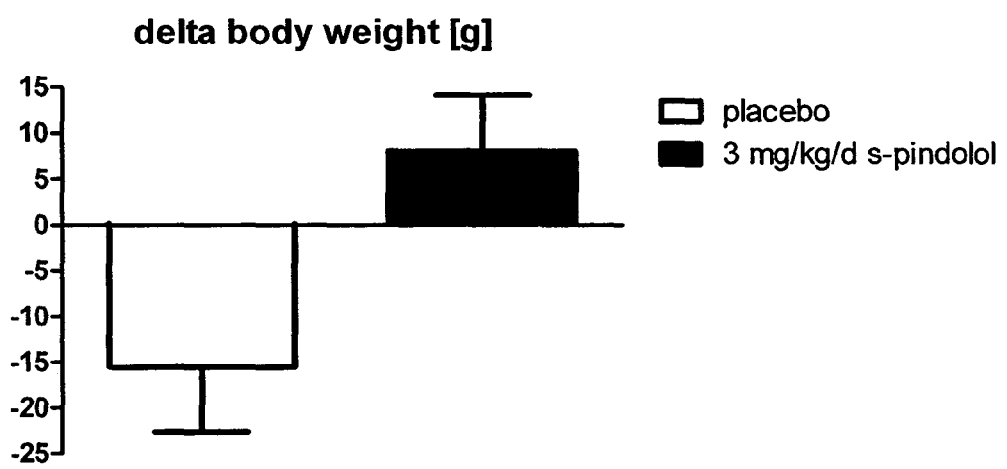

FIG. 4: change in body weight during the treatment period, p=0.02.

Figure 5:
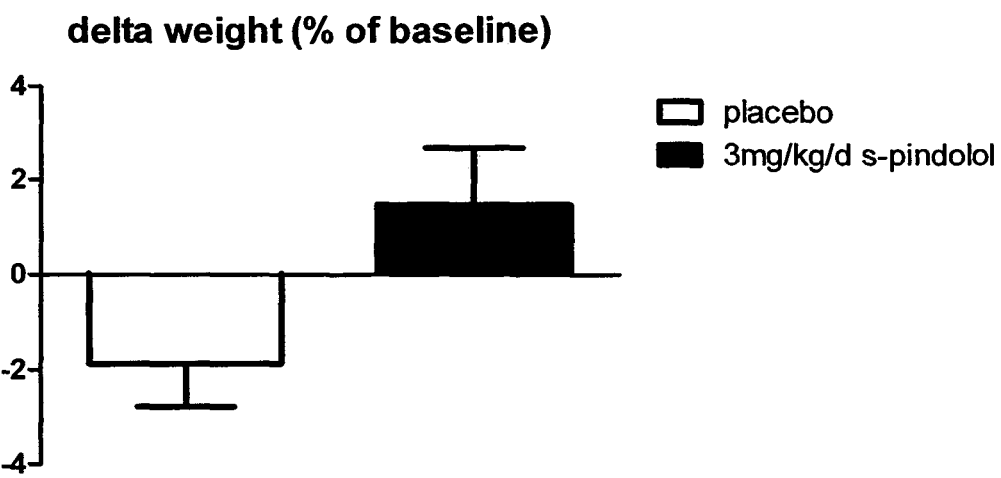

FIG. 5: change in body weight during the treatment period, p=0.026.

Figure 6:
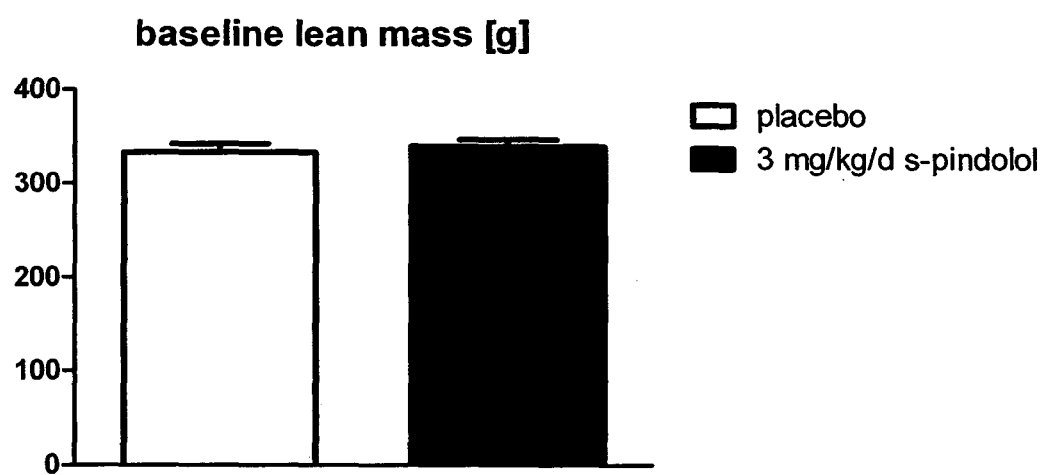

FIG. 6: lean body mass at baseline, p=0.58.

Figure 7:

FIG. 7: change in body weight during the treatment period, p=0.0002.

Figure 8:
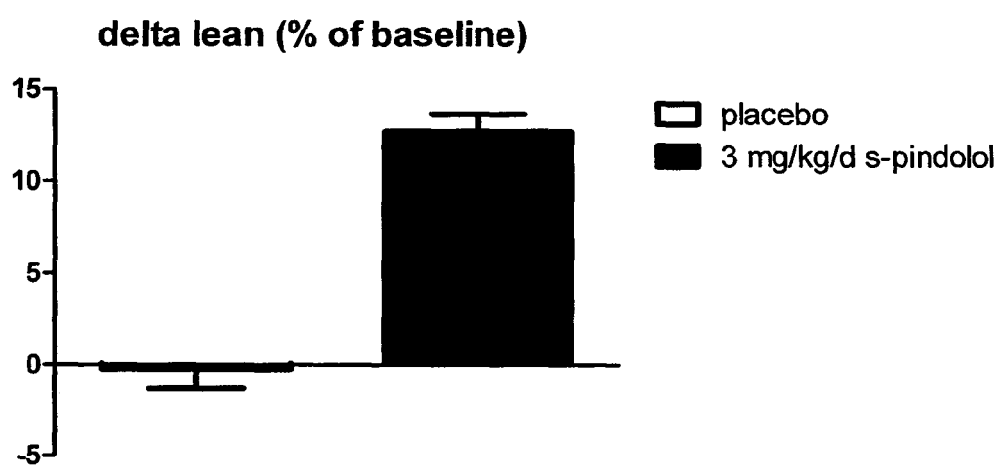

FIG. 8: change in body weight during the treatment period, p=0.0001.

EXAMPLE 1

Methods

Young, healthy, male Wistar Han rats (201.8±2.4 g) were housed in groups of two to three per cage under standard conditions. Animals were randomized to receive either 0.3 mg S-Pindolol/kg/d (n=5), 3 mg S-Pindolol/kg/d (n=5) or placebo (n=16) once daily per gavage for 16 days.

Body composition (lean mass) of the animals was analyzed using the EchoMRI-700 system (Echo Medical Systems, Houston, Tex., USA) before treatment and at the end of the study. Body weight was recorded before treatment and at the end of study. Organ weights were recorded at the end of study.

Results:

Body weight was significantly increased in animals treated with high dose S-Pindolol (FIG. 1). Lean body mass (i.e. muscle mass) was dose dependently increased by S-Pindolol (FIG. 2).

This effect was also seen in individual organ/tissue weights (table 1), where treatment with S-Pindolol shows a dose dependent increase in the weight of the gastrocnemius and tibialis muscles. Treatment has no effect on the spleen or the liver; hence the gain in lean mass can be attributed to skeletal muscle specifically. Judging from the percent increase weight in the soleus (slow twitch fibers) and the extensor digitalis longus (EDL; fast twitch fibers); it seems that S-Pindolol has a stronger effect on fast twitch fibers.

TABLE 1

Organ weight at the end of the study.

|  | Placebo | 0.3 mg/kg/d S-Pindolol | 3 mg/kg/d S-Pindolol |
| --- | --- | --- | --- |
| Gastrocnemius [mg] | 1234 ± 30 | 1420 ± 35** | 1492 ± 37*** |
| Tibialis [mg] | 447 ± 9 | 526 ± 15** | 535 ± 22* |

TABLE 1-continued

Organ weight at the end of the study.

|  | Placebo | 0.3 mg/kg/d S-Pindolol | 3 mg/kg/d S-Pindolol |
| --- | --- | --- | --- |
| Soleus [mg] | 97 ± 2 | 107 ± 2** (+10.3%) | 103 ± 3 (+6.2) |
| EDL [mg] | 104 ± 3 | 124 ± 6* (+19.2%) | 126 ± 4** (+21.1%) |
| Spleen [mg] | 639 ± 19 | 634 ± 14 | 622 ± 37 |
| Liver [mg] | 10454 ± 287 | 10156 ± 265 | 10568 ± 410 |

*p < 0.05,
**p < 0.01,
***p < 0.001.

EXAMPLE 2

Methods

Old, healthy, male Wistar Han rats (age 19 month, at the start of the experiment) were housed in groups of two to three per cage under standard laboratory conditions. Animals were randomized to receive either 3 mg/kg/d S-Pindolol/kg/d (n=8), or placebo (n=14) once daily per gavage for 28 days.

Body composition (lean mass) of the animals was analyzed using the EchoMRI-700 system (Echo Medical Systems, Houston, Tex., USA) before treatment, once per week during the study and at the end of the study. Body weight was recorded before treatment, once per week during the study and at the end of study. Organ weights were recorded at the end of study. One tibialis muscle per animals was dried at 60° C. for 48 h.

Results:

Total body weight and lean mass (i.e. skeletal muscle) were not different between placebo and 3 mg/kg/d S-Pindolol groups (FIGS. 3, 6). Body weight was significantly increased in animals treated with this high dose S-Pindolol (FIGS. 4, 5). Lean body mass (i.e. muscle mass) was increased by S-Pindolol (FIGS. 7, 8). Lean mass was increased by 12.7% compared to baseline in senile animals. Placebo treated animals lost 1.5% lean mass during the same period, which shows that aged rats actually develop sarcopenia.

The change in lean mass, was also similarly also seen in individual organ/tissue weights (table 2), where treatment with S-Pindolol showed a increase in the weight of the gastrocnemius, EDL and tibialis muscles, while the soleus weight did not change. Treatment had no effect on the spleen or the liver; hence the gain in lean mass can be attributed to skeletal muscle effects specifically. Judging from the percent difference weight in the soleus (slow twitch fibers) and the extensor digitalis longus (EDL; fast twitch fibers); it seems that S-Pindolol has a stronger effect on fast twitch fibers. Assessment of tibialis dry mass showed an increase in dry weight in proportion to the overall increase in wet mass, so that the ratio of water content to dry mass content was not altered by S-Pindolol.

TABLE 2

Organ weight at the end of the study.

|  | Placebo | 3 mg/kg/d S-Pindolol |
| --- | --- | --- |
| Gastrocnemius [mg] | 2283 ± 78 | 2914 ± 133** |
| Tibialis [mg] | 827 ± 34 | 1034 ± 46** |
| Tibialis dry mass [mg] | 227 ± 9 | 276 ± 12* |
| Tibialis dry mass [%] | 27.89 ± 0.78 | 27.12 ± 0.46 |
| Tibialis water [%] | 72.1 ± 0.78 | 72.88 ± 0.46 |
| Soleus [mg] | 181 ± 11 | 173 ± 9 |

TABLE 2-continued

Organ weight at the end of the study.

|  | Placebo | 3 mg/kg/d S-Pindolol |
|---|---|---|
| EDL [mg] | 197 ± 9 | 236 ± 5** |
| Spleen [mg] | 924 ± 46 | 1045 ± 84 |
| Liver [g] | 13.68 ± 0.74 | 13.98 ± 0.76 |

*p < 0.05,
**p < 0.01.

The invention claimed is:

1. A method of treating a patient exhibiting sarcopenia without cachexia, comprising administering to the patient in need thereof a therapeutically effective amount of S-pindolol.

2. The method of claim 1, wherein the patient is aged 60 years or older.

3. The method of claim 1 wherein the therapeutically effective amount is administered as a single dose.

4. The method of claim 1 wherein the therapeutically effective amount is administered in divided doses.

5. The method of claim 1, wherein a daily dose of 2.5 mg to 50 mg is administered.

6. The method of claim 5 wherein the daily dose is administered as a single dose.

7. The method of claim 5, wherein the daily dose is administered in divided doses.

8. The method of claim 1, wherein the S-pindolol is administered in a pharmaceutical formulation selected from the group consisting of tablets, capsules, liquid, oral solutions, oral suspensions, parenteral solutions, buccal melts, intravenous solutions, and topical application forms.

* * * * *